US00PP11040P

United States Patent [19]

Cunneen

[11] Patent Number: Plant 11,040

[45] Date of Patent: Aug. 24, 1999

[54] ARGYRANTHEMUM PLANT NAMED 'SUGAR AND ICE'

[75] Inventor: Thomas Michael Cunneen, New South Wales, Australia

[73] Assignee: University of Sydney Plant Breeding Institute, Cobbitty, Cobbitty, Australia

[21] Appl. No.: 08/938,606

[22] Filed: Sep. 26, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Melissa L. Kimball
*Attorney, Agent, or Firm*—C. A. Whealy

[57] ABSTRACT

A distinct cultivar of Marguerite Daisy plant named Sugar and Ice, characterized by its rounded, mounding and compact plant habit; early flowering; medium-sized anemone-type inflorescences; and pure white ray and bright yellow disc florets.

2 Drawing Sheets

The present invention relates to a new and distinct cultivar of Marguerite Daisy plant, botanically known as *Argyranthemum frutescens* and referred to by the cultivar name Sugar and Ice.

The new cultivar is a product of a planned breeding program conducted by the inventor in Cobbitty, New South Wales, Australia. The objective of the breeding program was to develop compact and freely-flowering Marguerite daisies that have large inflorescences with good form.

The new cultivar originated from a cross made by the inventor in 1993 of a seedling selection of *Argyranthemum frutescens* identified as number AB5003, as the male or pollen parent, with the *Argyranthemum frutescens* cultivar Prostrate Double Pink (not patented), as the female or seed parent. The cultivar Sugar and Ice was discovered and selected by the inventor as a flowering plant within the progeny of the stated cross in a controlled environment in Cobbitty, New South Wales, Australia. Compared to plants of the male parent, the selection number AB5003, plants of the new Marguerite Daisy have larger inflorescences. Compared to plants of the female parent, the cultivar Prostrate Double Pink, plants of the new Marguerite Daisy are more compact and differ in ray floret color and inflorescence form.

Asexual reproduction of the new cultivar by terminal cuttings taken in Macquarie Fields and Cobbitty, New South Wales, Australia, has shown that the unique features of this new Marguerite Daisy are stable and are reproduced true to type in successive propagations.

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Sugar and Ice' which distinguish 'Sugar and Ice' as a new and distinct cultivar:

1. Rounded, mounding and compact plant habit.
2. Numerous inflorescences per plant.
3. Early flowering.
4. Medium-sized anemone-type inflorescences.
5. Pure white ray and bright yellow disc florets.

Plants of the new Marguerite Daisy can be compared to plants of the cultivar Pearl (not patented). In side-by-side comparisons conducted in Cobbitty, New South Wales, Australia, plants of the new Marguerite Daisy were more compact and had larger inflorescences and leaves. In addition, plants of the cultivar Pearl have daisy-type inflorescences whereas plants of the new Marguerite Daisy have anemone-type inflorescences.

Plants of the new Marguerite Daisy can also be compared to plants of the cultivar Sugar Baby (U.S. Plant Pat. No. 10,298). In side-by-side comparisons conducted in Encinitas, Calif., plants of the new Marguerite Daisy were more compact, less spreading, less vigorous, and differed in inflorescence form. Additionally plants of the new Marguerite Daisy had larger leaves, larger inflorescences, and longer peduncles than plants of the cultivar Sugar Baby.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical container plant of 'Sugar and Ice'.

The photograph on the second sheet comprises a close-up view of typical inflorescences of 'Sugar and Ice'. Floret and foliage colors in the photographs may appear different from the actual colors due to light reflectance.

DETAILED BOTANICAL DESCRIPTION

The following observations, measurements and values describe plants grown in Encinitas, Calif., in a polyethylene-covered greenhouse with day and night temperatures averaging 24 and 15° C., respectively. Color references are made to The Royal Horticultural Society Colour Chart except where general terms of ordinary dictionary significance are used.

Botanical classification: *Argyranthemum frutescens* cultivar Sugar and Ice.

Parentage:

*Male or pollen parent.*—Seedling selection of *Argyranthemum frutescens,* identified as number AB5003.

*Female or seed parent.*—*Argyranthemum frutescens* cultivar Prostrate Double Pink (not patented).

Propagation:

*Type cutting.*—Terminal cuttings.

*Time to initiate and develop roots.*—Less than 10 days or about 14 days at temperatures of 26 or 18° C., respectively.

*Rooting habit.*—Numerous, fibrous, and freely branching.

Plant description:

*General appearance.*—Rounded, mounding and compact plant habit. Pinnatifid foliage and erect flower stems that hold the inflorescences above the foliage. Appropriate for various sizes and types of containers.

*Plant height.*—About 28 cm from soil level to top of inflorescences.

*Plant width.*—About 28 cm.

*Branching.*—Moderate branching, lateral branch develop will be enhanced by removal of the terminal apex (pinching).

*Vigor.*—Moderately vigorous.

*Internode length.*—About 6.5 mm.

*Stem color.*—143C.

*Foliage description.*—Arrangement: Alternate, single. Shape: Pinnatifid. Apex: Acute. Base: Attenuate, sessile. Margin: Deeply incised. Length: About 9.5 cm. Width: About 4 cm. Texture: Glabrous and smooth. Durability to stresses: Good, very durable. Color: Young leaves, upper surface: 137C. Young leaves, lower surface: 137D. Mature leaves, upper surface: 137A. Mature leaves, lower surface: 137C. Venation, upper surface: 138B. Venation, lower surface: 137C.

Flowering description:

*Flowering habit.*—Single anemone-type composite inflorescence form. Inflorescences form at upper leaf axils. Florets arranged acropetally on a capitulum. Inflorescences last about four or five days.

*Quantity of inflorescences.*—Moderate to freely flowering, typically 4 to 6 flowers per lateral stem. Usually more than 20 inflorescences in flower per plant.

*Natural flowering season.*—Natural flowering season is spring to early fall. Plants flower continuously during this period.

*Inflorescence diameter.*—About 4 cm.

*Inflorescence depth* (*height*).—About 1.6 cm.

*Fragrance.*—None.

*Ray florets.*—Appearance: Satiny. Aspect: Initially flat then recurved as inflorescences develop. Shape: Elliptic. Apex: Irregular, bi and tri-dentate. Base: Attenuate. Margin: Entire. Length: About 1.8 cm. Width: About 6 mm. Texture: Smooth, glabrous. Color: When opening and mature, both surfaces: 155D. Number of ray florets per inflorescence: About 22 in two rows.

*Disc florets.*—Shape: Tubular, 5-parted and flared at apex. Diameter of disc: About 3.2 cm. Disc floret length: About 1.2 cm. Disc floret width: About 2 mm. Color: Immature: 154D. Mature: 155D at apex, 149B at base. Number of disc florets per inflorescence: Numerous, usually about 250.

*Phyllaries.*—Arrangement: Overlapping in alternate rows, tightly pressed to the receptacle. Length: About 9 mm. Diameter: About 1.2 mm. Shape: Elliptic.

*Peduncle.*—Length, first peduncle: About 7.8 cm. Length, fourth peduncle: About 9.4 cm. Strength: Very strong and erect, inflorescences held above foliage. Texture: Smooth. Color: 144B.

*Flower bud.*—Shape: Spherical. Length: About 9 mm. Diameter: About 9 mm. Color: 146D.

*Androecium.*—None observed on ray or disc florets.

*Gynoecium.*—Present on ray and disc florets. Pistil number: One per floret. Pistil length: About 3 mm. Style length: About 2.5 mm. Style color: 12C. Stigma shape: Bipartate. Stigma color: 12A. Ovary color: 1D.

Disease resistance: No resistance to fungal, bacterial or viral pathogens has been noted.

Seed production: Seed production is typically not observed.

It is claimed:

1. A new and distinct Marguerite Daisy plant named 'Sugar and Ice', as illustrated and described.

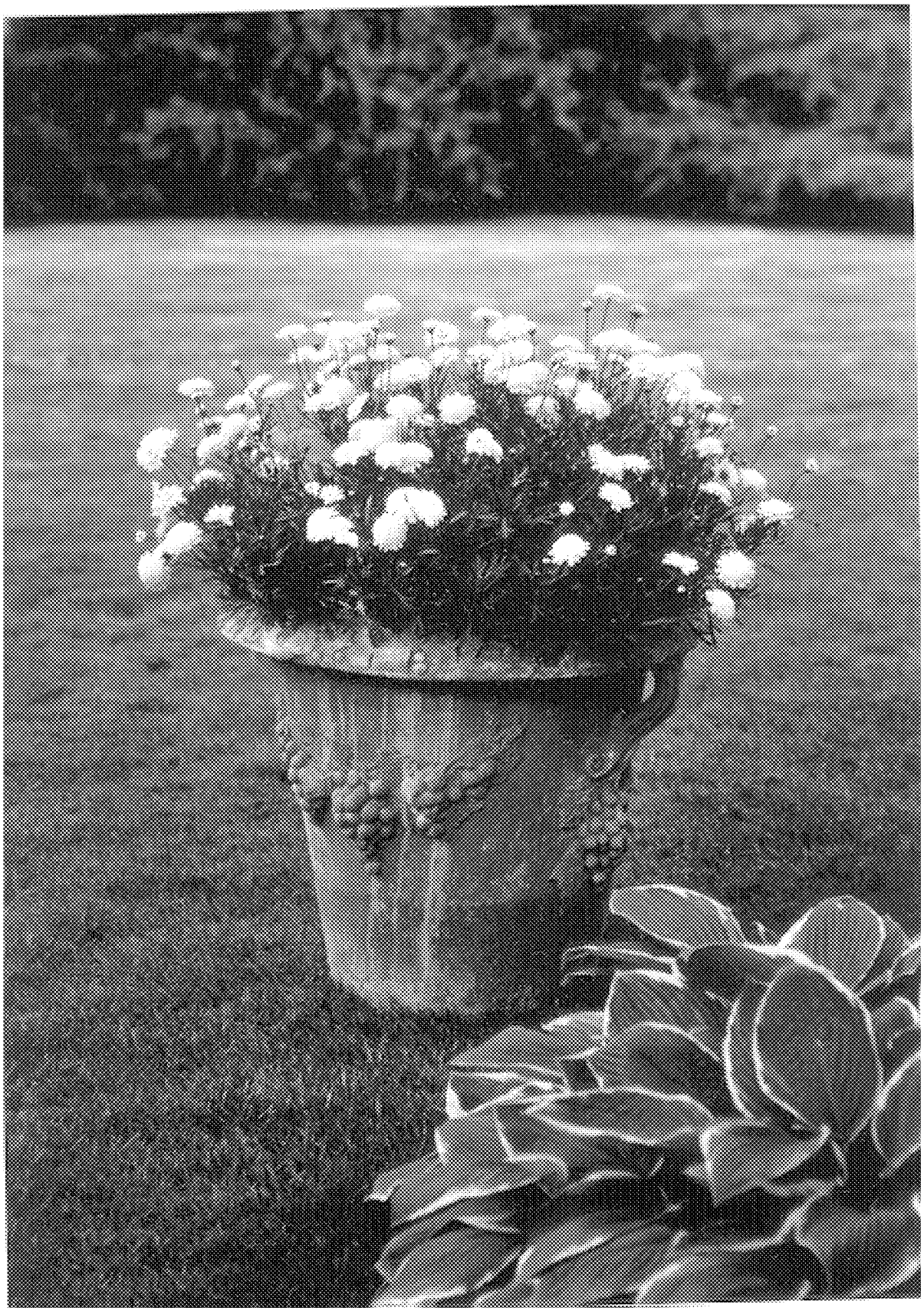

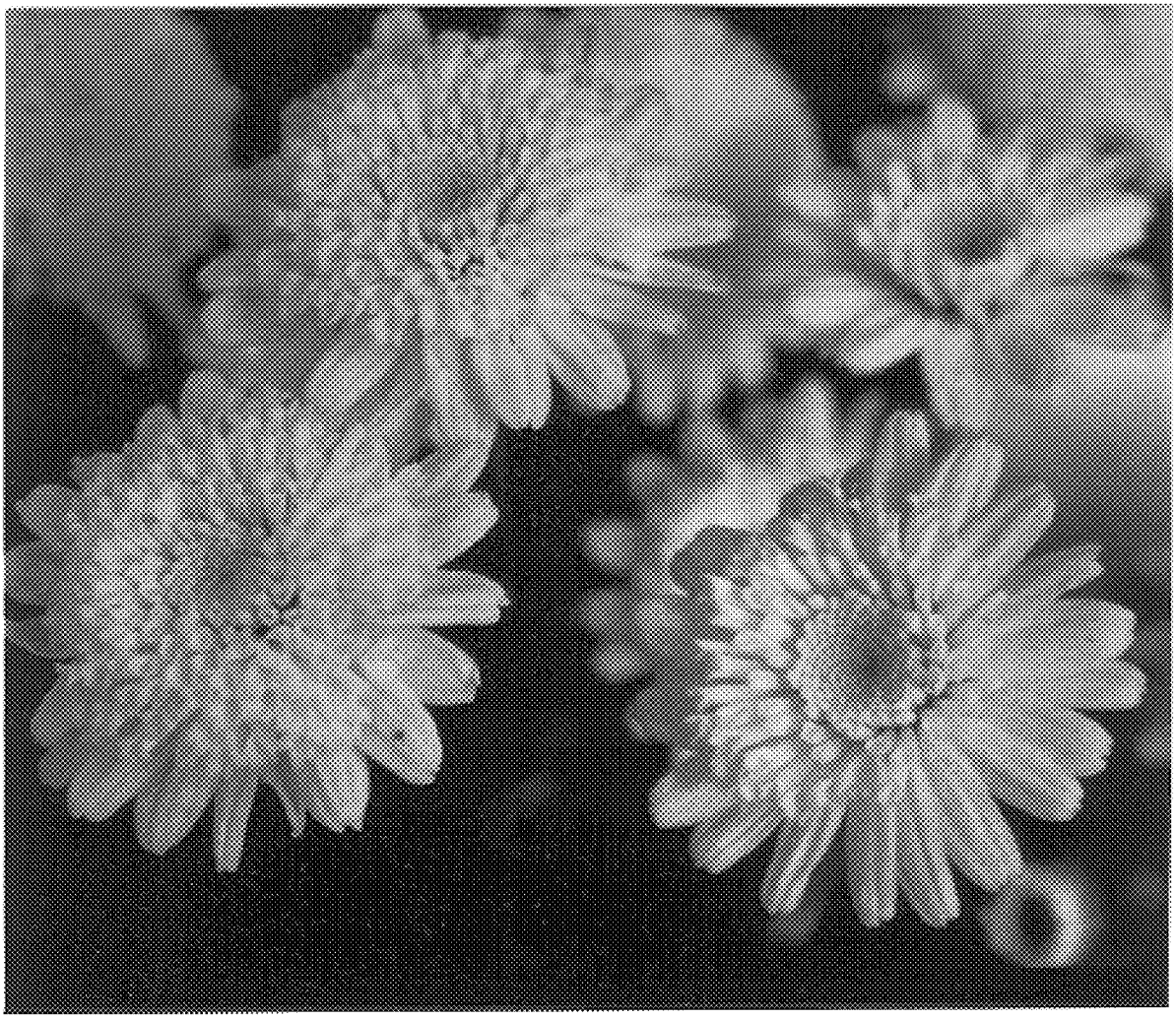

* * * * *